United States Patent
Karkare et al.

(10) Patent No.: US 10,925,503 B2
(45) Date of Patent: Feb. 23, 2021

(54) SATURATION-TOLERANT ELECTROPHYSICAL RECORDING INTERFACE

(71) Applicant: The Regents of the University of California, Oakland, CA (US)

(72) Inventors: Vaibhav Karkare, San Jose, CA (US); Dejan Markovic, Palo Alto, CA (US)

(73) Assignee: The Regents of the University of California, Oakland, CA (US)

(*) Notice: Subject to any disclaimer, the term of this patent is extended or adjusted under 35 U.S.C. 154(b) by 931 days.

(21) Appl. No.: 15/037,595

(22) PCT Filed: Nov. 19, 2014

(86) PCT No.: PCT/US2014/066449
§ 371 (c)(1),
(2) Date: May 18, 2016

(87) PCT Pub. No.: WO2015/077362
PCT Pub. Date: May 28, 2015

(65) Prior Publication Data
US 2016/0287121 A1 Oct. 6, 2016

Related U.S. Application Data

(60) Provisional application No. 61/905,955, filed on Nov. 19, 2013.

(51) Int. Cl.
*A61B 5/04* (2006.01)
*H03K 3/03* (2006.01)
(Continued)

(52) U.S. Cl.
CPC ........ *A61B 5/04017* (2013.01); *A61B 5/0402* (2013.01); *A61B 5/0428* (2013.01);
(Continued)

(58) Field of Classification Search
CPC .............. A61B 5/04017; A61B 5/0428; H03K 3/0315; H03K 5/1565
See application file for complete search history.

(56) References Cited

U.S. PATENT DOCUMENTS 6,055,848 A 5/2000 Weigold
2002/0027478 A1* 3/2002 Sudou .................. H03K 3/0315
331/46

(Continued)

FOREIGN PATENT DOCUMENTS

AU     2014353079 B2    10/2018
EP        3072266 A1     9/2016
(Continued)

OTHER PUBLICATIONS

Extended European Search Report for European Application No. 14864109.5, Search completed Jun. 12, 2017, dated Jun. 19, 2017, 9 Pgs.
(Continued)

*Primary Examiner* — Son T Le
*Assistant Examiner* — Adam S Clarke
(74) *Attorney, Agent, or Firm* — KPPB LLP

(57) ABSTRACT

Signal recording sensor systems in accordance with embodiments of the invention include sensors capable of sensing and capturing electrophysiological signals in the presence of interference signals, an analog front-end including circuitry configured to record electrophysiological input signals as a voltage, and an analog to digital converter including a voltage-controlled-oscillator configured to convert the recorded analog electrophysiological input signal to a phase output. While such signal recording sensor systems can be used in the recording of biosignals and/or electrophysiological signals generated from living organisms, signal recording sensor systems in accordance with embodiments of the
(Continued)

invention are not limited to recording biosignals and/or electrophysiological signals.

20 Claims, 10 Drawing Sheets

(51) Int. Cl.
*A61B 5/0476* (2006.01)
*A61B 5/0488* (2006.01)
*A61B 5/0428* (2006.01)
*A61B 5/0402* (2006.01)
*H03K 5/156* (2006.01)

(52) U.S. Cl.
CPC .......... *A61B 5/0476* (2013.01); *A61B 5/0488* (2013.01); *H03K 3/0315* (2013.01); *H03K 5/1565* (2013.01)

(56) References Cited

U.S. PATENT DOCUMENTS

| | | | |
|---|---|---|---|
| 2004/0097802 A1 | 5/2004 | Cohen | |
| 2008/0079485 A1 | 4/2008 | Taipale et al. | |
| 2008/0191767 A1* | 8/2008 | Koo | H03K 5/1565 327/175 |
| 2009/0251184 A1* | 10/2009 | Park | H03K 5/13 327/175 |
| 2010/0130139 A1* | 5/2010 | Panikkath | H03L 7/08 455/76 |
| 2010/0194484 A1* | 8/2010 | Deguchi | H03K 3/02315 331/17 |
| 2010/0312188 A1* | 12/2010 | Robertson | A61B 5/0006 604/156 |
| 2011/0066054 A1 | 3/2011 | Yazicioglu et al. | |
| 2012/0154192 A1 | 6/2012 | Op 'T Eynde | |
| 2012/0194369 A1 | 8/2012 | Galton et al. | |
| 2012/0328065 A1* | 12/2012 | Burg | H03L 7/113 375/376 |
| 2013/0069780 A1 | 3/2013 | Tran et al. | |
| 2013/0102266 A1* | 4/2013 | Kitsunezuka | H03D 7/1441 455/263 |
| 2014/0043562 A1* | 2/2014 | Kikuchi | H02M 3/156 349/61 |
| 2016/0211856 A1* | 7/2016 | Muhammad | H03M 1/0626 |

FOREIGN PATENT DOCUMENTS

| | | |
|---|---|---|
| EP | 3072266 B1 | 1/2019 |
| JP | 2001500618 A | 1/2001 |
| JP | 2012055588 A | 3/2012 |
| WO | 2015077362 A1 | 5/2015 |

OTHER PUBLICATIONS

Bohorquez et al., "A Biomedical Sensor Interface With a sinc Filter and Interference Cancellation", IEEE Journal of Solid-State Circuits, vol. 46, Issue 4, Apr. 2011, pp. 746-756, DOI: 10.1109/JSSC. 2011.2108128, Date of Publication: Feb. 24, 2011.

Daniels et al., "All-digital differential VCO-based A/D conversion", Proceedings of 2010 IEEE International Symposium on Circuits and Systems, May 30-Jun. 1, 2010, Paris, France, pp. 1085-1088.

Iwata et al., "Scalable Routing Strategies for Ad Hoc Wireless Networks", IEEE Journal on Selected Areas in Communications, vol. 17, Issue 8, Aug. 1999, pp. 1369-1379, DOI: 10.1109/49. 779920.

Kim et al., "A digital-intensive receiver front-end using VCO-based ADC with an embedded 2nd-Order anti-aliasing Sinc filter in 90nm CMOS", 2011 IEEE International Solid-State Circuits Conference, Feb. 20-24, 2011, San Francisco, CA, USA, pp. 176-178.

Raiteri et al., "An organic VCO-based ADC for quasi-static signals achieving 1LSB INL at 6b resolution", 2013 IEEE International Solid-State Circuits Conference Digest of Technical Papers, Feb. 17-21, 2013, San Francisco, CA, USA, pp. 108-109.

International Preliminary Report on Patentability for International Application PCT/US2014/066449, Report issued May 24, 2016, dated Jun. 6, 2016, 7 Pgs.

International Search Report and Written Opinion for International Application PCT/US2014/066449, Completed Feb. 24, 2015, dated Feb. 25, 2015, 9 pgs.

"Pipelined ADCs and More", EE247 Lecture 22, Power Point, UC Berkeley, Retrieved from: https://inst.eecs.berkeley.edu/~ee247/fa09/ files07/lectures/L22_2_f09.pdf, 2009.

Gao et al., "HermesE: A 96-Channel Full Data Rate Direct Neural Interface in 0.13μm CMOS", IEEE Journal of Solid-State Circuits, vol. 47, No. 4, Apr. 2012, pp. 1043-1055.

Ghosh, Abhishek "Signal Processing Techniques Enabling Wideband A/D Converters", University of California Los Angeles, Doctor of Philosophy in Electrical Engineering, Dissertation, 2013, 119 pgs.

Straayer, Matthew "VCO-based ΣΔ ADC Design Examples", Retrieved from: http://www.cppsim.com/Tutorials/vco_adc_tutorial.pdf, 2008, 24 pgs.

Taylor et al., "A Mostly-Digital Variable-Rate Continuous-Time Delta-Sigma Modulator ADC", IEEE Journal of Solid-State Circuits, vol. 45, No. 12, Dec. 2010, pp. 2634-2646.

Yazicioglu et al., "A 30μW Analog Signal Processor ASIC for biomedical signal monitoring", Solid-State Circuits Conference Digest of Technical Papers (ISSCC), 2010 IEEE International, Feb. 7-11, 2010, pp. 124-125.

Zou et al., "A 1V 22μW 32-Channel Implantable EEG Recording IC", IEEE International Solid-State Circuits Conference (ISSCC), Digest of Technical Papers, 2010, pp. 126-127.

Zou et al., "A 1-V 450-nW Fully Intergrated Programmable Biomedical Sensor Interface Chip", IEEE Journal of Solid-State Circuits, vol. 44, Issue 4, Apr. 2009, pp. 1067-1077.

Daniels et al., "All-digital differential VCO-based A/D conversion", Proceedings of 2010 IEEE International Symposium on Circuits and Systems, May 30-Jun. 2, 2010, Paris, France, pp. 1085-1088, DOI: 10.1109/ISCAS.2010.5537342.

Kim et al., "A digital-intensive receiver front-end using VCO-based ADC with an embedded 2nd-Order anti-aliasing Sinc filter in 90nm CMOS", 2011 IEEE International Solid-State Circuits Conference, Feb. 20-24, 2011, San Francisco, CA, pp. 176-178, DOI: 10.1109/ ISSCC.2011.5746271.

* cited by examiner

SATURATION-TOLERANT ELECTROPHYSICAL RECORDING INTERFACE

GOVERNMENT LICENSE RIGHTS

This invention was made with Government support under 0847088, awarded by the National Science Foundation (EDISON). The Government has certain rights in the invention.

FIELD OF THE INVENTION

The present invention generally relates to recording sensors that record signals, such as electrophysiological signals, in the presence of large interferers with minimal saturation.

BACKGROUND

Sensing weak signals in the presence of large interferers is a problem encountered in many applications. For instance, long-term wireless recording of electrophysiological signals such as EEG, ECG, and EMG in day-to-day use, outside of a well-controlled clinical and/or laboratory setting can enable effective remote healthcare and open new avenues for biomedical research. To allow operation in potentially noisy remote locations, electrophysiological-recording systems typically record low-amplitude signals (~100 µVp) in the presence of large (~100 µmVp), non-stationary interferers like motion artifacts, unrelated biological signals, and various man-made interferers. This situation is not exclusive to remote environments and is also encountered in various clinical and laboratory applications such as the presence of motion artifacts in sleep EEG recordings, the presence of parental ECG in a fetal ECG recording, or the large stimulation artifact in neural action potential recordings. Being non-stationary in nature, these interferers often spill into the signal band and typically cannot be filtered out by conventional frequency-selective filters. Most existing electrophysiological-recording systems are prone to saturation and, hence, cannot operate in such noisy environments.

As shown by conventional recording interface 100 of FIG. 1, traditional electrophysiological-recording front-ends (AFEs) include amplifiers that have a high voltage gain (40 dB to 80 dB) to amplify the weak received signals to ~1V for digitization by an ADC such as SAR. Incorporation of a high-gain, low-noise stage causes the noise of the following stages in the signal chain to be insignificant and allows a biosignal sensor to be designed with low input-referred noise without paying a hefty price in power consumption.

High signal gain can be looked at as a key enabler to achieving low input-referred noise. However, the high gain implies a low saturation-free dynamic range (~60 dB), causing the AFE to saturate due to a few mVs of interferers. A few systems palliate the problem by allowing the AFE to recover quickly from saturation, such as the systems described in H. Gao, et al. "HermesE: A 96-Channel Full Data Rate Direct Neural Interface in 0.13 µm CMOS," IEEE JSSC, vol. 47, no. 4, pp. 1043-1055, April 2012.

SUMMARY OF THE INVENTION

Signal recording sensor systems in accordance with embodiments of the invention include sensors capable of sensing and capturing signals in the presence of interference signals, an analog front-end including circuitry configured to record electrophysiological input signals, and an analog to digital converter including a voltage-controlled-oscillator configured to convert the recorded analog input signal to a phase output. In several embodiments, at least one input signal includes an electrophysiological signal. While such signal recording sensor systems can be used in the recording of biosignals and/or electrophysiological signals generated from living organisms, signal recording sensor systems in accordance with embodiments of the invention are not limited to recording biosignals and/or electrophysiological signals.

In many embodiments, the analog to digital converter further includes a differential voltage-controlled-oscillator. In multiple embodiments, the differential voltage-controlled-oscillator is configured to be duty-cycled according to a particular duty-cycling ratio.

In some embodiments, the voltage-controlled-oscillator is a differential voltage-controlled-oscillator configured to be duty-cycled according to a particular duty-cycling ratio and the analog to digital converter further includes a timing sequence for harmonic-mode suppression. In several embodiments, the timing sequence for harmonic-mode suppression includes (1) a first timing signal at which oscillator nodes of the differential voltage-controlled-oscillator are pre-charged to deterministic values and (2) a second timing signal at which a high-voltage pulse is applied to a fixed location of the differential voltage-controlled-oscillator. In some embodiments, the timing sequence for harmonic-mode suppression includes a dynamic element matching implementation. In several embodiments, the dynamic element matching implementation includes a pseudo-random dither between a first timing signal and a second timing signal in the timing sequence for harmonic-mode suppression. In some of said several embodiments, the first timing signal is when a voltage pulse is injected in the differential voltage-controlled-oscillator and the second timing signal is when a counting process for the differential voltage-controlled-oscillator is started.

The voltage-controlled-oscillator can include a front end that provides opposite polarity inputs to two ring oscillators. Thus, for each conversion, the input can be digitized twice with opposite polarities. In many embodiments, the digital output signal is subject to a first-order digital high-pass filter prior to final digital output. In multiple embodiments, the system further includes a polynomial correction engine that is configured to perform polynomial fits on the digital output.

In some embodiments, the sensor system further includes coarse and fine counting circuits. The coarse and fine counting circuits of some embodiments is configured to generate a fine count based on (1) initial and final locations on the voltage-controlled-oscillator identified during a period and (2) the polarity of a transitioning inverter in the voltage-controlled-oscillator. The coarse and fine counting circuits of some embodiments is configured to generate a coarse count based on a number of periods of the voltage-controlled-oscillator.

Systems of many embodiments are configured to receive varying types of signals. For instance, in some embodiments the analog front-end is further configured to record the at least one input signal as a voltage. In said some embodiments, the analog to digital converter can be further configured to convert the recorded analog input signal to a current output prior to converting the recorded analog input signal to the phase output. In addition, several embodiments of the analog front-end are configured to record the at least one input signal as a current. Moreover, in many embodiments, at least one sensor includes an environmental sensor and at least one input signal can include an environmental signal.

Signal recording sensor systems in accordance with multiple embodiments of the invention include sensors capable of sensing and capturing electrophysiological input signals in the presence of interference signals, an analog front-end including circuitry configured to record the electrophysiological input signals as voltages, and an analog to digital converter including a differential voltage-controlled-oscillator configured to convert the recorded analog electrophysiological input signals to phase outputs. In said multiple embodiments, the differential voltage-controlled-oscillator is configured to be duty-cycled according to a particular duty-cycling ratio, the differential voltage-controlled-oscillator is configured to operate according to a timing sequence for harmonic-mode suppression that utilizes a set of timing signals. The set of timing signals includes (1) a first timing signal at which oscillator nodes of the differential voltage-controlled-oscillator are pre-charged to deterministic values, and (2) a second timing signal at which a high-voltage pulse is applied to a fixed location of the differential voltage-controlled-oscillator. In addition, the signal recording sensor systems in accordance with said multiple embodiments of the invention include a coarse and fine counting circuitry configured to generate a fine count based on (1) initial and final locations on the differential voltage-controlled-oscillator identified during a period and (2) the polarity of a transitioning inverter in the differential voltage-controlled-oscillator, and to generate a coarse count based on a number of periods of the voltage-controlled-oscillator.

DETAILED DESCRIPTION OF THE DRAWINGS

Turning now to the drawings, systems and methods for implementing electrophysiological-recording systems that utilize phase-domain recording in order to recover electrophysiological signals even in the presence of substantial non-stationary interferers. Phase-domain recording can record measured differences in phases to separate interfering signals that would saturate low-voltage signals. Such phase-domain recording can be of particular utility in recording biosignals generated from living organisms as biosignals are often low-voltage and occur in the presence of substantial interfering signals. Utilizing phase-domain recording enables embodiments of the invention to tolerate saturation in the presence of 200 mVp-p interferers, enables reconfigurability to support various invasive and/or non-invasive bio-signals, and/or retain similar power consumption, noise, and area to conventional electrophysiological-recording systems.

Figure 1:
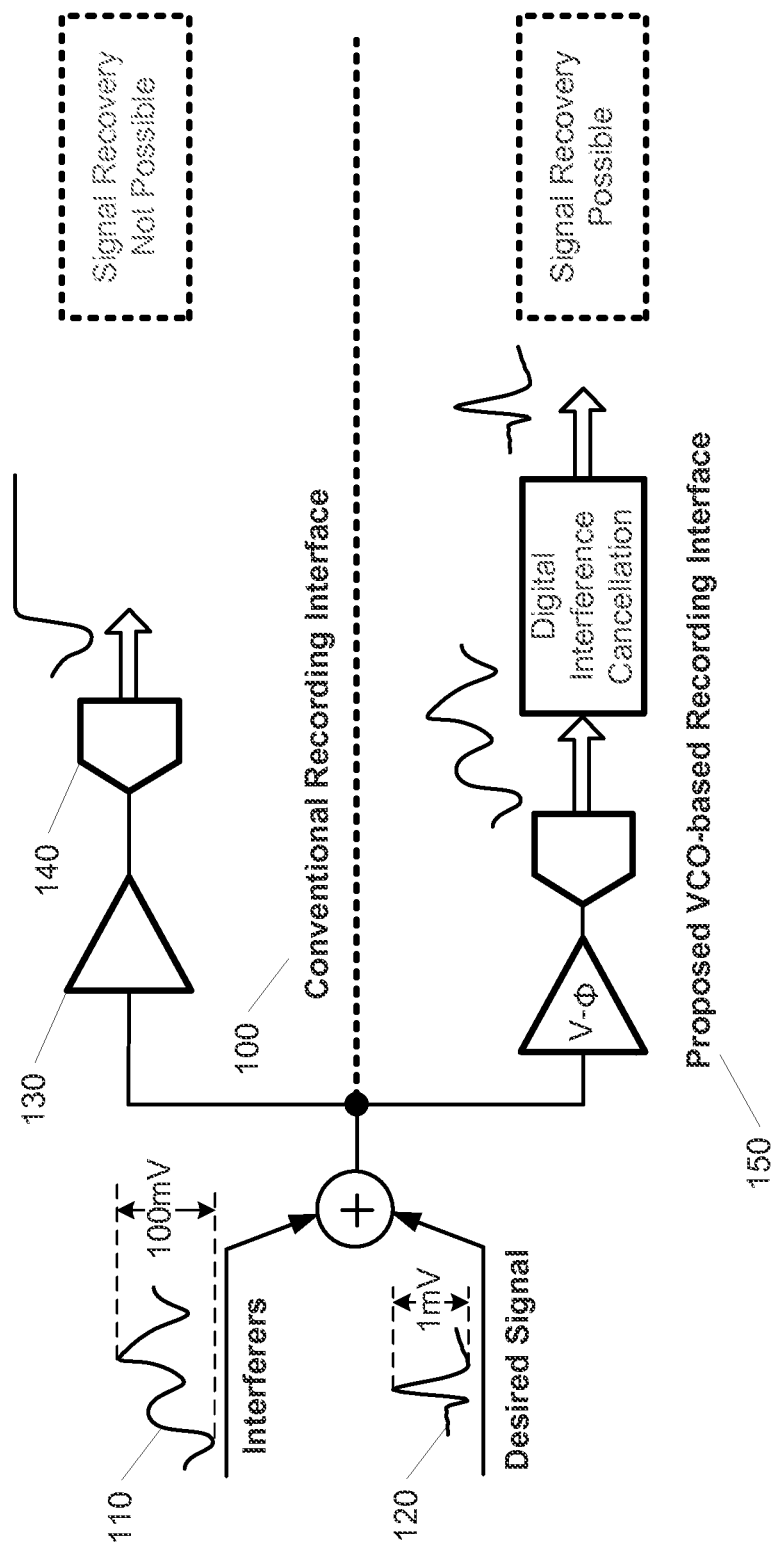
FIG. 1 conceptually illustrates a phase-domain signal recording system in accordance with an embodiment of the invention along with a conventional recording interface.

FIG. 1 conceptually illustrates a phase-domain signal recording system 150 in accordance with an embodiment of the invention along with a conventional recording interface 100. Both conventional recording interface 100 and phase-domain signal recording system 150 are shown receiving a composition of two signals. The two signals include interferers 110 and desired signal 120. Desired signal 120 can include (but is not limited to) EEG recordings, EMG recordings, ECG recordings, neural action potential recordings, environmental signals, signals that need to be sensed for the Internet of Things (IoT) applications, and/or other weak signals. Interferers 110 can include (but are not limited to) non-stationary interferers like motion artifacts, unrelated biological signals, and various man-made interferers. Embodiments of the invention can recover a desired signal 120 that is less than 10 µVp in the presence of larger amplitude signals ranging up to 200 mVp. Being non-stationary in nature, interferers such as interferers 110 often spill into the signal band and are difficult to filter out by conventional frequency-selective filters that are typically utilized in a conventional recording interface 100.

As shown in FIG. 1, conventional recording interface 100 has an amplifier 130 and/or Analog to Digital Convertor 140. Typically, amplifier 130 will be a high voltage gain amplifier. Consequently, the conventional recording interface 100 will typically saturate for large interferers, leaving no hope for signal recovery. In phase-domain signal recording system 150, the signal is processed in the phase domain to avoid signal saturation under the presence of these large, non-stationary interferers. Embodiments of the invention, such as phase-domain signal recording system 150, can implement a voltage-to-phase conversion gain in order to prevent saturation and maintain a low input-referred noise for signal recordings.

Previous signal recording systems have yielded saturation toleration ranges of 1-10 mVp-p interferers. In contrast, phase-domain signal recording systems in accordance with embodiments of the invention have demonstrated saturation tolerance in excess of 10 mVp-p interferers and up to 200 mVp-p interferers. Such saturation tolerance is of particular utility in sensing and recording various biosignals, such as (but not limited to) EEG, ECG, EMG, and/or AP+LFP. In addition, embodiments of the invention support duty-cycling to allow for reconfiguration to adjust to varying power and/or signal requirements. These and further embodiments will be discussed below.

Voltage-Controlled-Oscillator Based Analog to Digital Convertors in Recording Systems Phase-domain signal recording systems in accordance with many embodiments of the invention utilize Voltage-Controlled-Oscillator (VCO) in conjunction with Analog to Digital Convertors (ADC) in recording signals. VCO-ADCs can receive recording signals from various types of analog sensors. For instance, VCO-ADCs in accordance with embodiments of the invention can receive input from analog sensors for voltage, analog sensors for current, various environmental signal sensors, biosignal sensors, electrophysiological sensors, signals from sensors for environments of devices and/or things, and/or other weak analog signal sensors. Various embodiments of the invention and their utilization of VCO-ADCs to digitize such sensed input signals will be discussed in conjunction with several figures below.

Figure 2A:
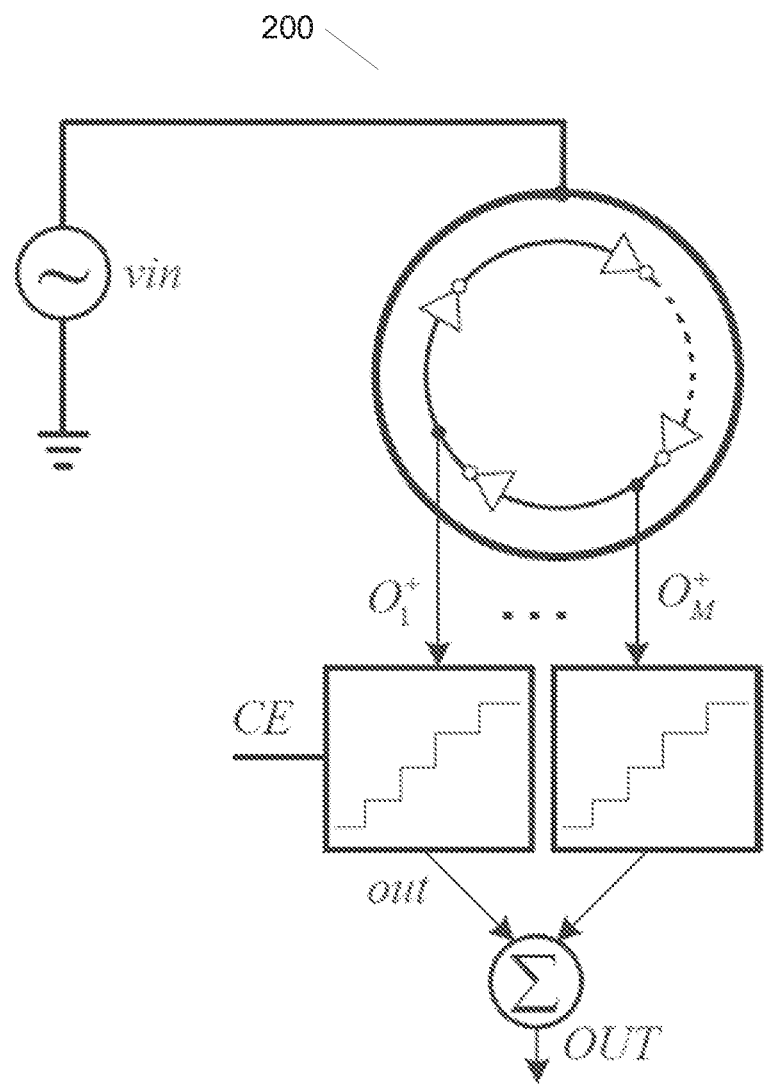
FIG. 2A conceptually illustrates a Voltage-Controlled-Oscillator (VCO) based Analog to Digital Convertor (ADC) in accordance with an embodiment of the invention.

FIG. 2A conceptually illustrates a Voltage-Controlled-Oscillator (VCO) based Analog to Digital Convertor (ADC) 200 in accordance with an embodiment of the invention. VCO-ADCs use voltage-to-phase conversion for digitizing input. VCO-ADCs can be used for their quantization-noise shaping properties. However, many embodiments of the invention utilize VCO-ADCs to provide saturation-tolerance and robustness against interferers in signal recordings. VCO-ADCs can use voltage-to-phase conversion for digitizing the input. In several embodiments, the VCO-ADC 200 quantizes the phase increment of a VCO in a given time period.

While the embodiment illustrated in FIG. 2A encompasses a voltage-to-phase conversion, different embodiments may include different inputs and sub-operations in generating phase output. For instance, several embodiments include an intermediate conversion of initial voltage input to a current stage prior to final conversion of the current stage to the phase output. Such intermediate conversions occur within the VCO of said several embodiments. Moreover, different embodiments may initially receive different types of initial input. For instance, in some embodiments the analog front-end can initially record a current input and then utilize a current-to-phase conversion for digitizing the current-based input.

Figure 2B:
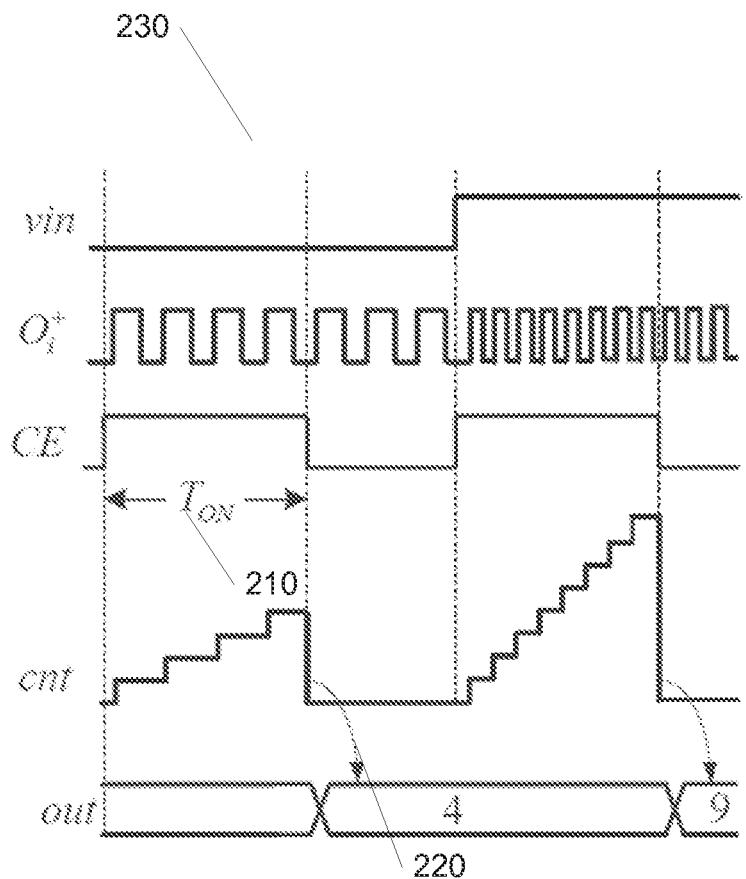
FIG. 2B conceptually illustrates a timing diagram associated with a VCO-ADC in accordance with an embodiment of the invention.

FIG. 2B conceptually illustrates a timing diagram 340 associated with VCO-ADC 200. As shown in timing diagram 230, the resolution provided by VCO-ADC 200 depends on the ratio of the counting period ($T_{ON}$) 210 and the propagation delay of an inverter 220. Given the low gate delays afforded by modern Complementary Metal-Oxide-Semiconductor (CMOS) processes and the relatively low sampling-rate requirements of biosignals and/or electrophysiological signals, the resolution provided by VCO-ADC 200 is sufficient to support direct digitization of biosignals and/or electrophysiological signals. Other, low-voltage signals that are not biosignals and/or electrophysiological signals can also be directly digitized by VCO-ADCs in accordance with embodiments of the invention.

Differential VCO-ADCs in Recording Systems

Figure 3A:
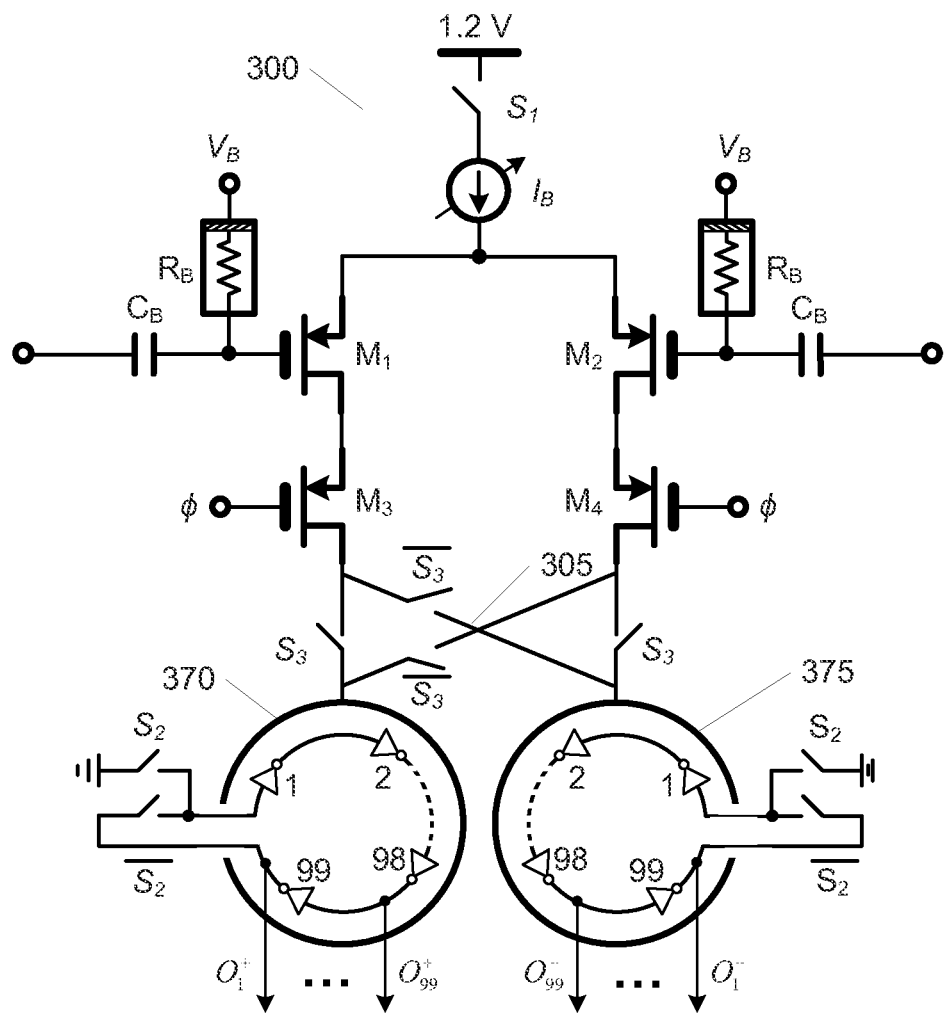
FIG. 3A conceptually illustrates a differential VCO-ADC topology in accordance with an embodiment of the invention.

FIG. 3A conceptually illustrates a differential VCO-ADC topology 300 in accordance with an embodiment of the invention. Differential VCO-ADC topology 300 includes a duty-cycled VCO-based signal recording front end 305 and twin 99-stage ring oscillators 370 and 375. Front end 305 adjusts polarities of input signals such that twin 99-stage ring oscillators 370 and 375 each receive opposite polarities of input. In some embodiments, front ends may provide a same signal in opposite polarities to the twin ring oscillators. Thus, the signal may be digitized twice with opposite polarities for each conversion to phase output. Differential VCO-ADCs in accordance with embodiments of the invention can meet the power supply rejection ratio (PSRR) and common-mode rejection ratio (CMRR) requirements of electrophysiological recording systems and/or other weak signal recording systems. PSRR describes the amount of noise from a power supply that a particular device can reject. CMRR is the rejection by a device of unwanted common-mode input signals and/or interferers relative to the desired difference signal. A tradeoff can exist between power consumption and sampling rates in designing signal recording systems. For instance, a reconfigurable system where the oscillator sensitivity and hence the power consumption is chosen for the fastest sampling rates can have a degraded power efficiency for the lower sampling rates. Also, a differential topology imposes an inherent power versus input range tradeoff. This power versus input range tradeoff can lead to a higher power consumption for supporting a higher input range. The potential power requirement increase can be circumvented by duty-cycling the VCO-ADC.

A. Duty Cycling Differential VCO-ADCs

Differential VCO-ADC topology 300 supports duty-cycling to reduce power requirements and provide reconfigurability. The power and/or signal requirements of differential VCO-ADC topology 300 can readily be reconfigured by adjusting the duty-cycling ratio of VCO-ADC topology 300. For instance, different duty-cycling ratios can be selected in order to target different types and/or levels of signals. However, in a circuit with a duty-cycled system, the noise contribution of the input devices can increase as the duty-cycling ratio is reduced. This increase in the input-device noise contribution limits the minimum duty-cycling ratio used to 5-15%. In experimental results, the differential VCO-ADC topology 300 achieved an input-referred noise of 2.14 µVrms in the 0.1 Hz to 200 Hz band with a 10% duty-cycling ratio. While duty-cycled VCO-ADCs in accordance with embodiments of the invention can be readily reconfigured to support varying signal and/or power requirement, duty-cycling a ring VCO can excite harmonic modes during startup, which can lead to large errors at the output.

B. Limiting Excitation of Harmonic Modes of Duty-Cycled VCO-ADCs

Figure 3B:
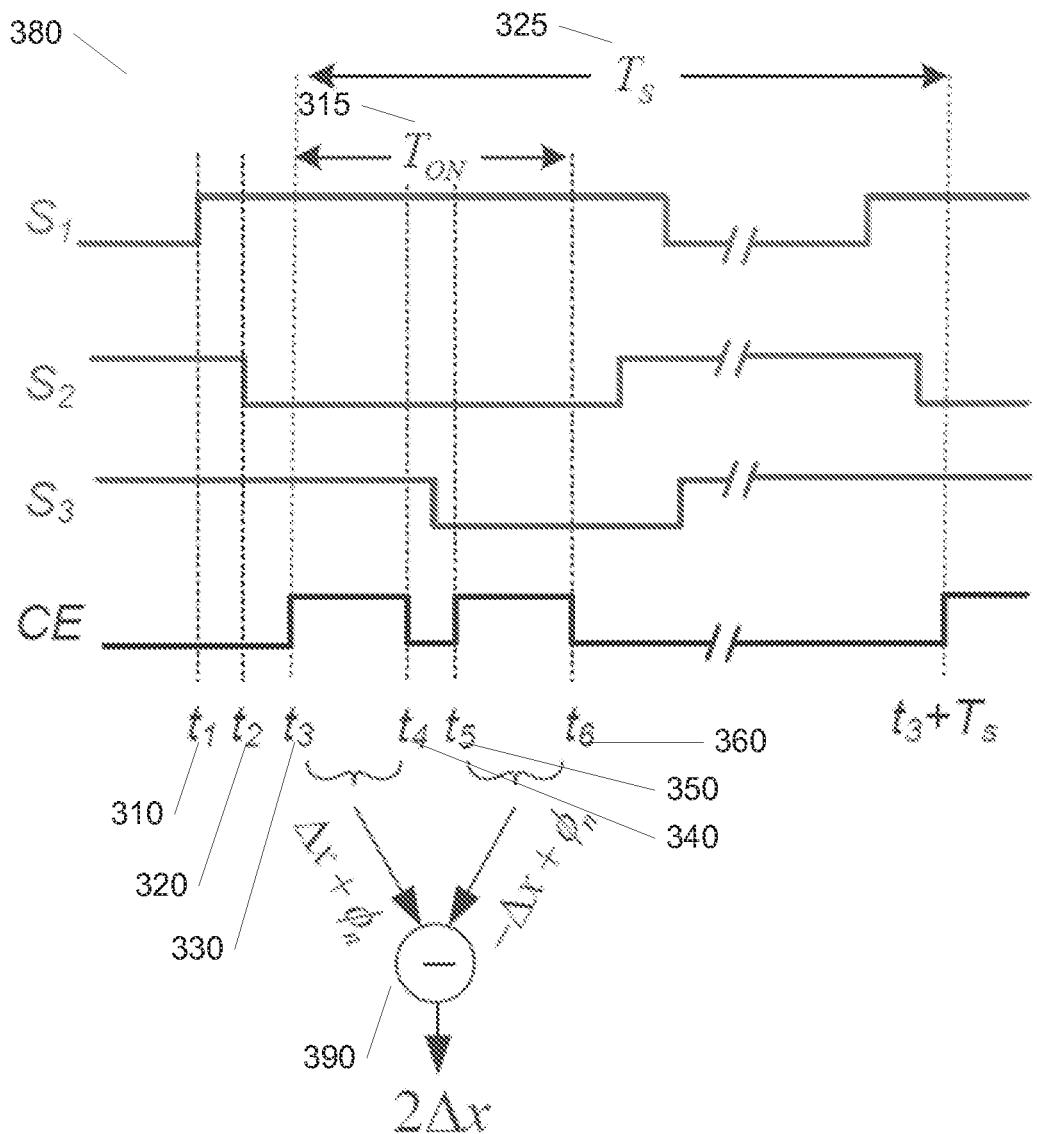
FIG. 3B conceptually illustrates a timing sequence for harmonic-mode suppression in accordance with an embodiment of the invention.

In order to limit the excitation of harmonic modes during startup phases in duty-cycled VCO-ADCs, embodiments of the invention can provide for timing sequences that serve to suppress harmonic modes. FIG. 3B conceptually illustrates a timing sequence for harmonic-mode suppression 380 in accordance with an embodiment of the invention. The timing sequence for harmonic-mode suppression 380 includes several signal timings t1 310, t2 320, t3 330, t4 340, t5 350, and t6 360. In addition, timing sequence for harmonic-mode suppression 380 also shows two periods, counting period $T_{on}$ 315 and cycle period $T_s$ 325. In the embodiment illustrated in FIG. 3B, signals are recorded during counting period $T_{on}$ 315 and the timing sequence for harmonic-mode suppression 380 recycles according to cycle period $T_s$ 325. Counting period includes recorded timing signals t3 330, t4 340, t5 350, and t6 360. Other embodiments may utilize different timings as necessary to implement the invention.

The timing sequence for harmonic-mode suppression 380 can prevent harmonic oscillation modes in VCO-ADCs by pre-charging the oscillator nodes at time t1 310 to deterministic values, followed by injecting a high-voltage pulse at a fixed location in the ring at time t2 320. The large voltage pulse at time t2 320 and the appropriately charged state nodes ensure that only the fundamental oscillation mode prevails in the VCO-ADC, avoiding large errors that can occur in a duty-cycled VCO-ADC.

However, the deterministic location of the injected pulse can destroy the barrel-shift dynamic-element matching (DEM) inherent to a VCO-ADC and may cause significant nonlinearity. In order to correct for this, an explicit DEM is implemented in the sequence for harmonic-mode suppression 380 illustrated in FIG. 3B by adding a pseudo-random dither to time t2 320 (at which the voltage pulse is injected in the ring) relative to the time t3 330 (at which the counting process is started). This DEM implementation randomizes the inverter ring mismatch without adding any noise or sampling jitter to the signal path.

C. Reducing Low Frequency Phase Noise in VCO-ADCs

In order to digitize weak signals (such as electrophysiological signals and/or biosignals), input-referred noise from the VCO-ADC of less than 10 μVrms would be required. Accordingly, electrophysiological recording front ends should have an input-referred noise of less than 10 10 μVrms to provide for reliable acquisition of weak signals. This input-referred noise and/or low-frequency phase noise can dominate the noise of the VCO-ADC. The front end 305 and twin 99-stage ring oscillators 370 and 375 shown in FIG. 3A enable VCO-ADCs in accordance with embodiments of the invention to meet such a requirement by enabling two opposite polarity samplings of signals within a single sampling period. Specifically, front end 305 provides opposite polarities input signals to twin 99-stage ring oscillators 370 and 375. These two opposite polarity samplings of signals can be chopped together. As shown in FIG. 3B, a discrete-time implementation of chopping is used to further suppress the low-frequency phase noise. For each conversion, the input is digitized twice, with opposite polarities in the twin 99-stage ring oscillators 370 and 375. The double digitization in differential VCO-ADC topology 300 correspond to periods t3 330 to t4 340 and t5 350 to t6 360 in timing sequence for harmonic-mode suppression 380. A first-order digital high-pass filter 390 subsequently "down-converts" the chopped signal, providing an overall second-order high-pass shape to the phase noise contributed by the ring.

The above described techniques, timing, and/or components discussed in conjunction with differential VCO-ADC topology 300 and/or timing sequence for harmonic-mode suppression 380 can be used singularly, or in combination as required for any particular implementation of the invention. For instance, various combinations and sub-combinations of the above discussed matters can be used in differing embodiments of the invention while not departing from the spirit of the invention.

Correcting for Nonlinearity of VCO-ADCs in Signal Recording Systems

Figure 4:
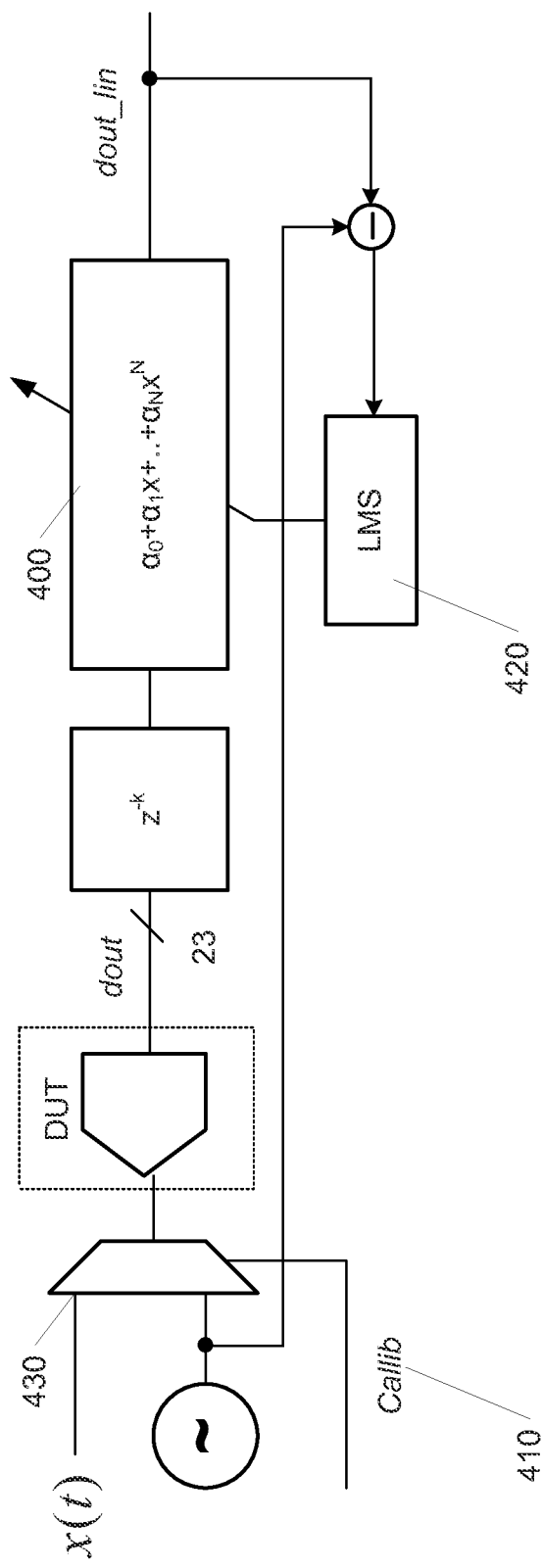
FIG. 4 conceptually illustrates a polynomial correction engine in accordance with an embodiment of the invention.

A VCO-ADC is inherently nonlinear by nature and typical VCO-ADCs can only provide 6-7 bits of linearity. In addition, embodiments of the invention utilizing injected pulses can introduce further sources of nonlinearity. This nonlinearity can arise from the differential pair and the oscillator tuning curve. In order to address the risk of significant nonlinearity, some embodiments employ a polynomial correction engine that performs polynomial fits to measured and ideal signal levels. FIG. 4 conceptually illustrates a polynomial correction engine 400 in accordance with an embodiment of the invention. Inputs from a signal generator are applied to the ADC in an adaptive foreground calibration phase 410, implemented at the receiver end. A Least-Mean Squared (LMS) loop 420 adaptively changes the coefficients of the correction polynomial to minimize the error between the ADC output and the expected ideal output. The polynomial correction engine 400 may not be subject to the stringent power constraints imposed on biosignal recording systems, because the calibration can be implemented as part of a receiving system in some embodiments. Various embodiments can utilize (or not utilize) the polynomial correction engine illustrated in FIG. 4 and/or any of a variety of correction engines including (but not limited to) any appropriate N-th order polynomial correction engine as necessary for the particular implementation of the invention.

Coarse and Fine Counting Logic

Figure 5A:
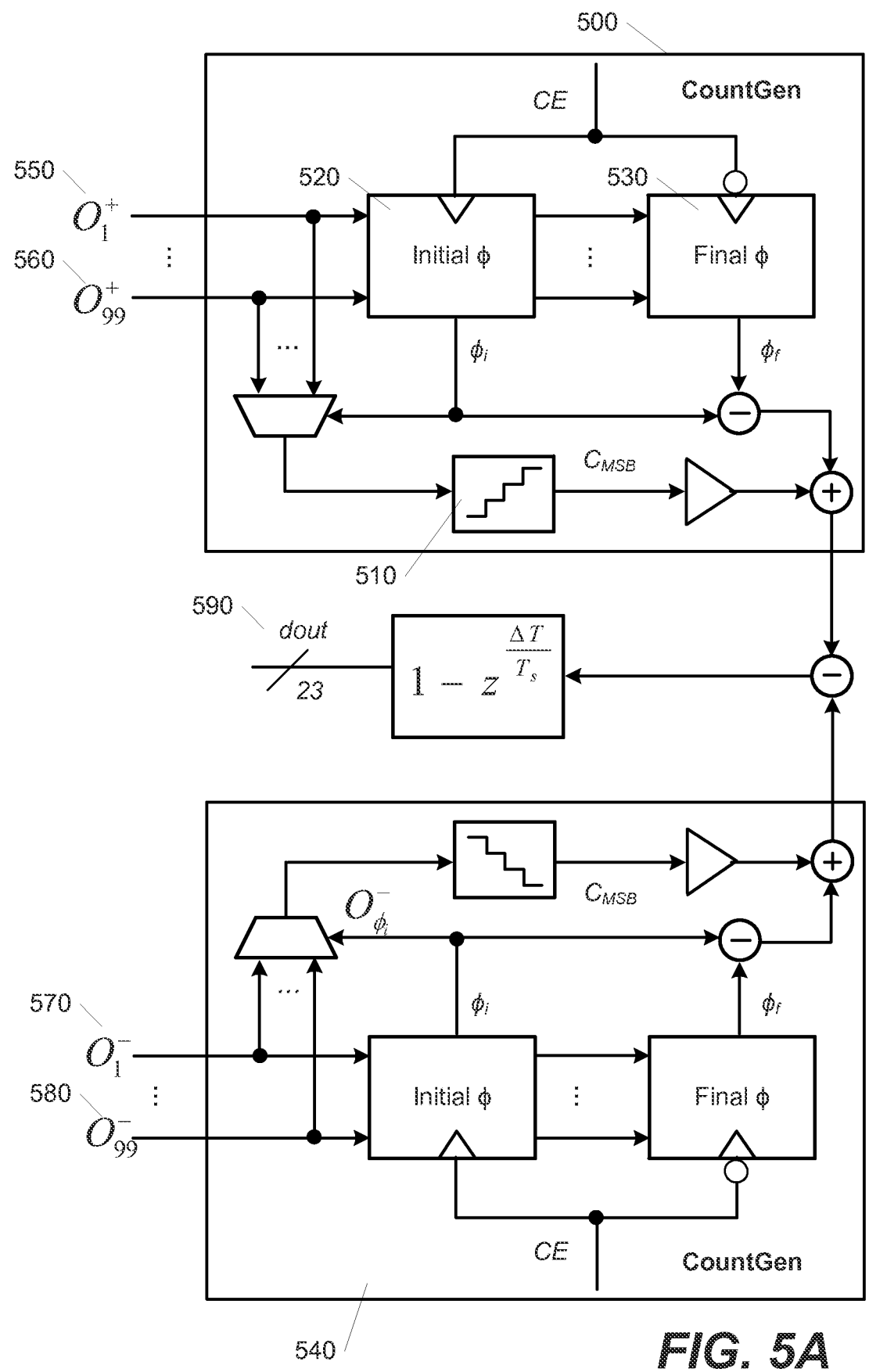
FIG. 5A conceptually illustrates an example coarse and fine counting circuit in accordance with an embodiment of the invention.
Figure 5B:
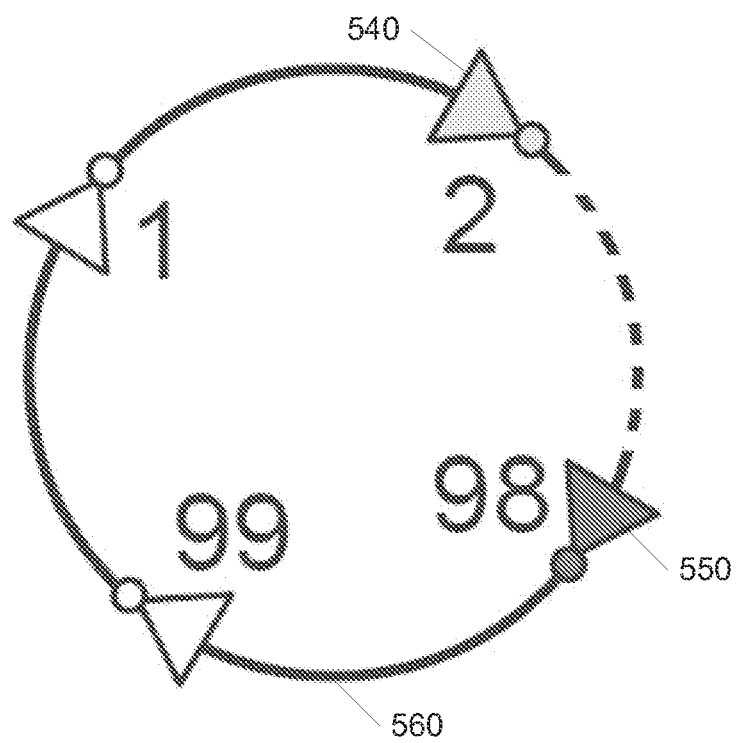
FIG. 5B conceptually illustrates a ring oscillator associated with a coarse and fine counting circuit in accordance with an embodiment of the invention.

Multiple embodiments provide for coarse and fine counting circuits that consume dramatically less power (~75× less power) than conventional techniques that utilize independent counters for each stage of the oscillator counting process. FIG. 5A conceptually illustrates an example coarse and fine counting circuit 500 along with a second course and fine counting circuit 540. As shown, coarse and fine counting circuit 500 includes a coarse counter 510, an initial state register 520, a final state register 530. Course and fine counting circuit 540 includes corresponding counters and registers to course and fine counting circuit 500. Coarse and fine counting circuit 500 receives signals through signal input channels 550 and 560. Coarse and fine counting circuit 550 receives signals through signal input channels 570 and 580. The output of circuits 500 and 540 is combined to generate a 23-bit output code 590. FIG. 5B conceptually illustrates a ring oscillator 560 associated with the coarse and fine counting circuits illustrated in FIG. 5A. In several embodiments, the ring oscillator 560 is a first voltage-controlled-oscillator of a VCO-ADC that includes a pair of twin ring oscillators. In such embodiments, the output from a first ring oscillator is directed to at least signal input channels 550 and 560 and the output from a second ring oscillator is directed to at least signal input channels 570 and 580.

Coarse and fine counting circuit 500 can count the intermediate phases of the ring oscillator 560 to maximize the resolution obtained for a given amount of power consumed by the oscillator. This is to be contrasted with typical techniques that would use an independent counter on each stage. Placing an independent counter on each stage could result in a steep power cost and consume a significant area on a biological sensor. Biological sensors typically have limited areas on which to place circuitry.

Coarse and fine counting circuit 500 provides comparable resolution to techniques with independent counters by splitting counting logic into a coarse and a fine stage. To avoid the costs associated with independent counters, coarse and fine counting circuit 500 includes split counting logic that is split into a coarse and a fine stage. The counting logic produces a 23-bit output code 590 using a single "coarse" counter 510 to count the integer number of periods (CMSB) and an initial state register 520 and a final state register 530 to generate a "fine" count based on (1) the initial ($\varphi i$) 540 and final ($\varphi f$) 550 locations on the ring oscillator 560 identified during a period and (2) the polarity of the transitioning inverter in the ring oscillator 560 illustrated in FIG. 5B. In addition, some embodiments use the initial state information of the ring oscillator 560 to determine the phase used for the "coarse" counter to mitigate against errors arising from cycle clips between the coarse and fine counts. This implementation of the coarse and fine counting circuit 500 can consume many times less power (up to 75× less power) compared to an implementation using independent counters for each stage. Various embodiments can utilize (or not utilize) the coarse and fine counting circuit 500 illustrated in FIG. 5A or an appropriate energy efficient counting circuit as necessary for the particular implementation of the invention.

Systems for Signal Recording Sensors

Figure 6:
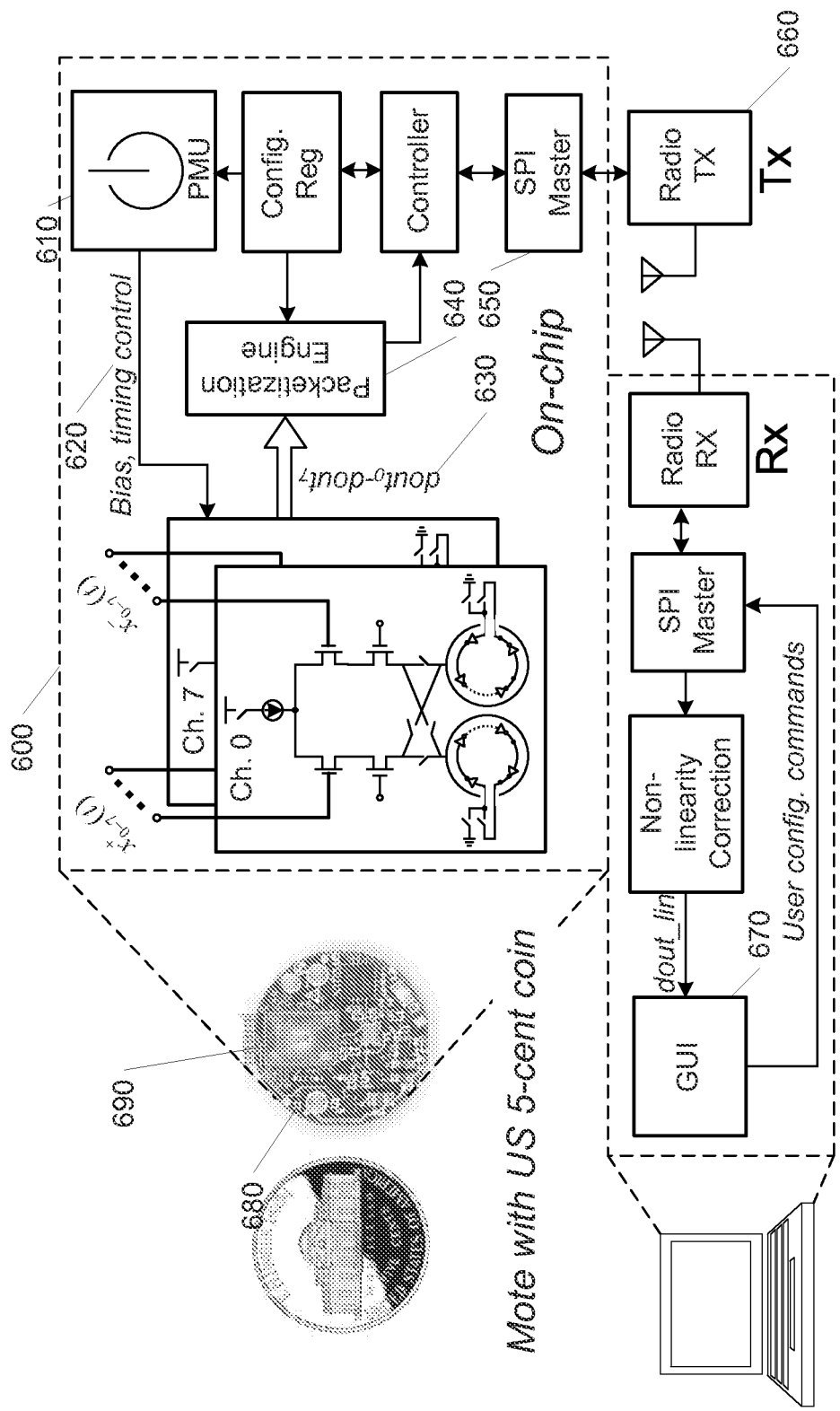
FIG. 6 conceptually illustrates a system-level block diagram of a signal recording sensor in accordance with an embodiment of the invention.

FIG. 6 conceptually illustrates a system-level block diagram of a signal recording sensor and interface 600 in accordance with an embodiment of the invention. The signal recording sensor and interface 600 can be implemented in a chip, and incorporated into miniature sensing platforms such as the nickels-zed mote 680. Timing and bias-current control signals for the ADC are generated from a crystal clock by a power-management module (PMU) 610. The crystal clock can use any of several commonly available crystal frequencies, such as (but not limited to) 16-MHz, 20-MHz, 24-MHz, and/or 48-MHz. Six-bit control words are used to provide a wide range of tuning for bias and timing control signals 620, allowing support for various signals of interest. As mentioned above, the signals of interest can include (but are not limited to) varying types of biosignals. In other embodiments, any of a variety of control words can be utilized as appropriate to the requirements of a specific application. In addition, bias and timing control signals 620 allows for support of both singular and simultaneous signals. The system-level block diagram 600 includes eight ADC channels 630 (dout0-dout7), whose outputs are packetized in real time at the packetization engine 640. Different embodiments may include different numbers of channels. The outputs of the eight ADC channels 630 (dout0-dout7) are packetized based on required sampling rates and the resolutions. The chip can also be used for less than 8 channels, without a significant power penalty, by disabling the undesired channels. The packetized data is communicated to an off-chip, wireless transceiver 660 through an SPI interface 650. All of the above configurations on the chip can be set wirelessly, in real time through a graphical user interface 670.

Different embodiments may be implemented on chips according to different processes and with different sizes and power consumptions. The following discussion is a specific example of implementing system-level block diagram 600 on a chip fabricated in a 65 nm CMOS process. In this example, implemented chips can occupy a total area of 2.77 mm$^2$ (front-end area of 0.16 mm$^2$/ch) and consume 770 nW/ch when recording a 2 mV$_{p-p}$ ECG signal, sampled at 250 Hz with a 2.5 µV$_{rms}$ input-referred noise and a 0.5 µV quantization step. Different implementations may occupy different areas, consumer different quantities of power, and sample at different frequencies without departing from the spirit of the invention. The implemented chip and the nRF24L01+transceiver can be mounted on a US nickel-sized mote 680, enabling electrophysiological recordings in an ambulatory setting. The chip can be used for human biosignal recordings such as (but not limited to) ambulatory human lead-II ECG recordings with wet electrodes, frontal-lobe EEG recordings with dry, over-the-hair electrodes, and surface EMG recordings from the biceps while jogging using dry electrodes. The specific mounting and packaging of the signal recording sensor system typically depends upon the requirements of a specific application in accordance with an embodiment of the invention.

Figure 7:
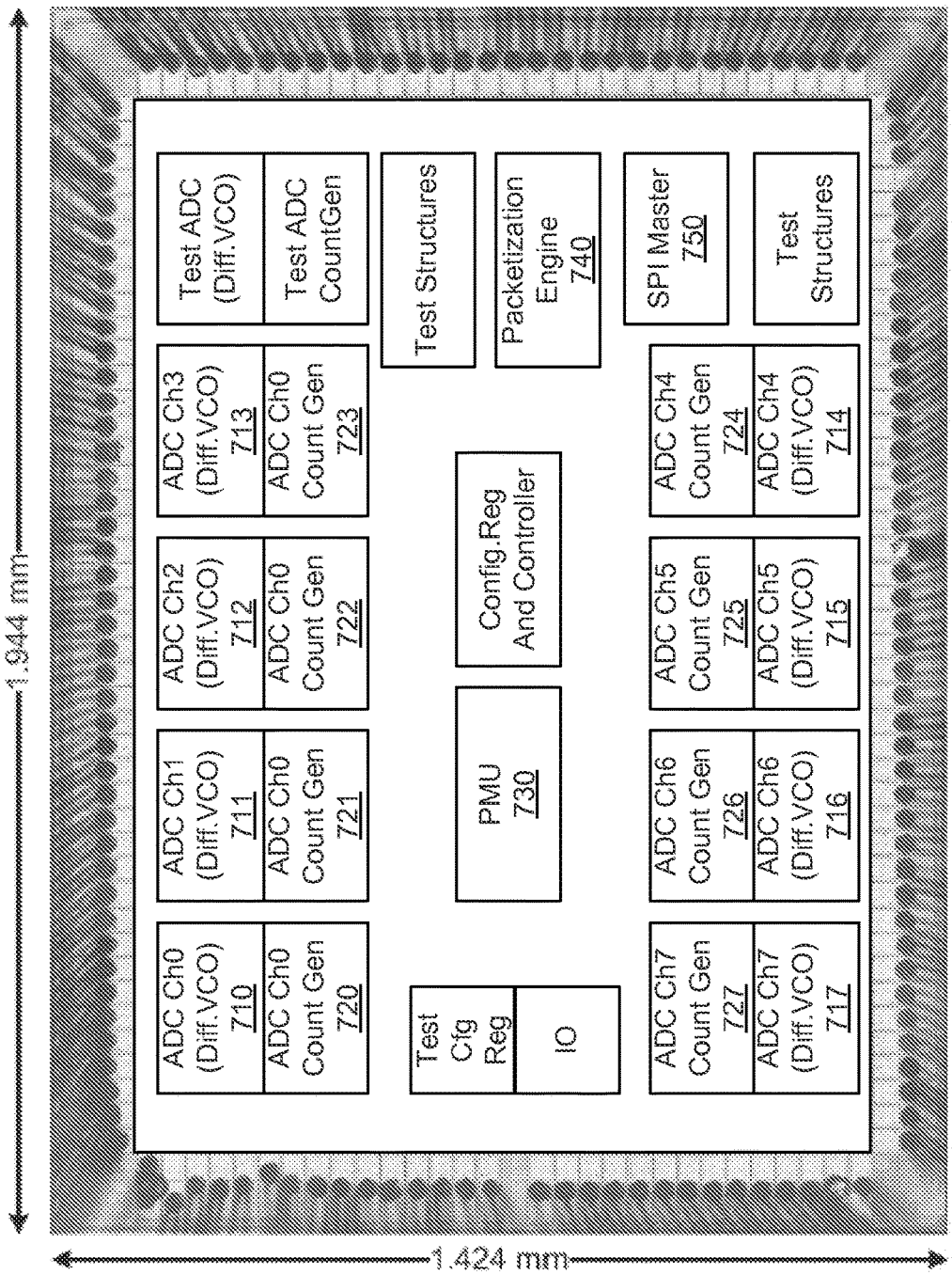
FIG. 7 conceptually illustrates a die micrograph of the circuitry of an embodiment of the invention.

Within the nickel-sized mote 680, a die micrograph of the circuitry associated with system-level block diagram 600 is illustrated. FIG. 7 conceptually illustrates a die micrograph 700 of the circuitry of an embodiment of the invention. As shown, die micrograph 700 includes many structures corresponding to the system-level blocks discussed above. Die micrograph 700 includes eight ADCs 710-717 (each with a differential VCO 720-727) providing eight channels numbered zero to seven. Die micrograph 700 also includes a power-management module (PMU) 730, a packetization engine 740, an SPI Master interface 750. Timing and bias-current control signals required for the ADC are generated from a 16-MHz crystal clock by power-management module (PMU) 730. Outputs of the eight ADC channels are packetized by the packetization engine 740 based on the required sampling rate and the resolution. Packetized data is communicated off-chip through SPI Master interface 750. The specific die micrograph illustrated in FIG. 7 is but one possible embodiment of the invention. Different embodiments may use different combinations and sub-combinations of components within the invention without departing from the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. For instance, while many embodiments of the invention are discussed in the context of biosignals and/or electrophysiological signals, such embodiments are not limited to biosignals and/or electrophysiological signals and can be utilized with any variety of input signal types. Thus, embodiments of the present invention should be considered in all respects as illustrative and not restrictive.

What is claimed is:

1. A signal recording sensor system comprising:
    at least one sensor capable of sensing at least one input signal in the presence of an interference signal, where the at least one sensor is configured to capture the at least one input signal;
    an analog front-end comprising circuitry configured to record the at least one input signal;
    an analog to digital converter comprising a voltage-controlled-oscillator configured to convert the recorded analog input signal to a phase output;
    wherein the voltage-controlled-oscillator is a differential voltage-controlled-oscillator configured to be duty-cycled according to a particular duty-cycling ratio, and
    wherein the voltage-controlled-oscillator is configured to select the particular duty-cycling ratio to target different types of signals within the signal recording sensor system.

2. The system of claim 1, wherein the at least one input signal comprises an electrophysiological signal.

3. The system of claim 1, wherein the analog to digital converter is further configured to operate according to a timing sequence for harmonic-mode suppression.

4. The system of claim 3, wherein the timing sequence for harmonic-mode suppression prevents harmonic oscillation modes utilizing a set of timing signals, and wherein the set of timing signals comprise:
    a first timing signal at which oscillator nodes of the differential voltage-controlled-oscillator are pre-charged to deterministic values; and
    a second timing signal at which a high-voltage pulse is applied to a fixed location of the differential voltage-controlled-oscillator.

5. The system of claim 3, wherein the timing sequence for harmonic-mode suppression includes a dynamic element matching implementation.

6. The system of claim 5, wherein the dynamic element matching implementation comprises the addition of a pseudo-random dither between a first timing signal and a second timing signal in the timing sequence for harmonic-mode suppression.

7. The system of claim 6, wherein:
    the first timing signal is when high-voltage pulse is applied to a fixed location of the differential voltage-controlled-oscillator; and the second timing signal is when a counting process for the differential voltage-controlled-oscillator is started.

8. The system of claim 1, wherein the differential voltage-controlled-oscillator comprises a front end that provides opposite polarity inputs to two ring oscillators.

9. The system of claim 1, wherein the digital output signal is subject to a first-order digital high-pass filter prior to final digital output.

10. The system of claim 1, wherein the system further comprises a polynomial correction engine that is configured to perform polynomial fits on the digital output.

11. The system of claim 1, wherein the sensor system further comprises coarse and fine counting circuitry.

12. The system of claim 11, wherein the coarse and fine counting circuitry is configured to generate a fine count based on (1) initial and final locations on the voltage-controlled-oscillator identified during a period and (2) the polarity of a transitioning inverter in the voltage-controlled-oscillator.

13. The system of claim 11, wherein the coarse and fine counting circuitry is configured to generate a coarse count based on a number of periods of the voltage-controlled-oscillator.

14. The system of claim 1, wherein the analog front-end is further configured to record the at least one input signal as a voltage.

15. The system of claim 1, wherein the analog to digital converter comprising the voltage-controlled-oscillator is further configured to convert the recorded analog input signal to a current output prior to converting the recorded analog input signal to the phase output.

16. The system of claim 1, wherein the analog front-end comprising circuitry is further configured to record the at least one input signal as a current.

17. The system of claim 1, wherein the at least one sensor comprises an environmental sensor, and wherein the at least one input signal comprises an environmental signal.

18. The system of claim 1, wherein the differential voltage-controlled-oscillator is duty-cycled to reduce power requirements.

19. The system of claim 1, wherein the duty-cycling ratio is at least 5%.

20. A signal recording sensor system comprising:
at least one sensor capable of sensing at least one electrophysiological input signal in the presence of an interference signal, where the at least one sensor is configured to capture the at least one electrophysiological input signal;
an analog front-end comprising circuitry configured to record the at least one electrophysiological input signal as a voltage;
an analog to digital converter comprising a differential voltage-controlled-oscillator configured to convert the recorded analog electrophysiological input signal to a phase output,
wherein the differential voltage-controlled-oscillator is configured to be duty-cycled according to a particular duty-cycling ratio,
wherein the differential voltage-controlled-oscillator is configured to operate according to a timing sequence for harmonic-mode suppression that utilizes a set of timing signals, the set of timing signals comprising:
a first timing signal at which oscillator nodes of the differential voltage-controlled-oscillator are pre-charged to deterministic values, and
a second timing signal at which a high-voltage pulse is applied to a fixed location of the differential voltage-controlled-oscillator; and
a coarse and fine counting circuitry configured to:
generate a fine count based on (1) initial and final locations on the differential voltage-controlled-oscillator identified during a period and (2) the polarity of a transitioning inverter in the differential voltage-controlled-oscillator, and
generate a coarse count based on a number of periods of the voltage-controlled-oscillator.

* * * * *